United States Patent
Hall et al.

(10) Patent No.: US 11,554,250 B2
(45) Date of Patent: Jan. 17, 2023

(54) SINGLE AND MULTILAYER BANDS AND RELATED METHODS

(71) Applicant: Merit Medical Systems, Inc., South Jordan, UT (US)

(72) Inventors: John William Hall, North Salt Lake, UT (US); Craig Nordhausen, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 1043 days.

(21) Appl. No.: 15/783,692

(22) Filed: Oct. 13, 2017

(65) Prior Publication Data

US 2018/0104019 A1 Apr. 19, 2018

Related U.S. Application Data

(60) Provisional application No. 62/409,608, filed on Oct. 18, 2016.

(51) Int. Cl.
| | |
|---|---|
| *A61M 25/01* | (2006.01) |
| *A61B 90/00* | (2016.01) |
| *A61B 17/00* | (2006.01) |
| *A61M 25/09* | (2006.01) |
| *A61M 25/10* | (2013.01) |
| *A61B 5/06* | (2006.01) |

(52) U.S. Cl.
CPC ......... *A61M 25/0108* (2013.01); *A61B 90/39* (2016.02); *A61M 25/0105* (2013.01); *A61B 5/064* (2013.01); *A61B 2017/00867* (2013.01); *A61B 2090/3966* (2016.02); *A61B 2562/12* (2013.01); *A61M 2025/09166* (2013.01); *A61M 2025/1079* (2013.01); *A61M 2205/32* (2013.01)

(58) Field of Classification Search
CPC ................ A61B 5/064; A61B 2562/12; A61B 2017/00867; A61B 90/39; A61B 2090/3966; A61M 25/0105; A61M 25/0108; A61M 2025/1079; A61M 2025/09166; A61M 2205/32
USPC ........................................................ 600/424
See application file for complete search history.

(56) References Cited

U.S. PATENT DOCUMENTS

| | | | |
|---|---|---|---|
| 5,045,071 A | * | 9/1991 | McCormick ...... A61M 16/0484 604/529 |
| 5,485,667 A | | 1/1996 | Kleshinski |
| 6,277,108 B1 | | 8/2001 | McBroom et al. |
| 8,021,418 B2 | | 9/2011 | Gerberding et al. |

(Continued)

FOREIGN PATENT DOCUMENTS

| | | |
|---|---|---|
| WO | 2005089664 | 9/2005 |
| WO | 2008124306 | 10/2008 |

OTHER PUBLICATIONS

International Search Report and Written Opinion dated Jan. 16, 2018 for PCT/US2017/056603.
European Search Report dated May 18, 2020 for EP17861384.0.

*Primary Examiner* — Hien N Nguyen
(74) *Attorney, Agent, or Firm* — Dorsey & Whitney LLP

(57) ABSTRACT

Medical appliances including reinforcing bands and radiopaque marker bands are disclosed. In some embodiments, bands may comprise two or more material layers. A first layer may control the mechanical properties of a multilayered marking band, and a second layer may exhibit greater radiopacity than the first layer. Bands may also comprise a single layer.

9 Claims, 2 Drawing Sheets

(56) References Cited

U.S. PATENT DOCUMENTS

| | | | |
|---|---|---|---|
| 2003/0125711 A1 | 7/2003 | Eidenschink et al. | |
| 2005/0021046 A1* | 1/2005 | Bilge | A61M 25/0068 606/108 |
| 2005/0215874 A1* | 9/2005 | Wang | A61M 25/0108 600/407 |
| 2005/0261760 A1* | 11/2005 | Weber | A61P 7/02 623/1.38 |
| 2006/0064159 A1* | 3/2006 | Porter | A61M 1/3661 623/1.24 |
| 2006/0116752 A1* | 6/2006 | Norton | D04C 1/06 623/1.34 |
| 2006/0129045 A1* | 6/2006 | Warnack | A61F 2/958 600/435 |
| 2007/0043429 A1* | 2/2007 | Hegel | A61F 2/82 623/1.15 |
| 2008/0243069 A1* | 10/2008 | Krivoruchko | A61L 31/088 604/103.1 |
| 2010/0217276 A1* | 8/2010 | Garrison | A61M 1/3659 606/128 |
| 2012/0046575 A1* | 2/2012 | Brown | A61M 25/09 600/585 |
| 2013/0096658 A1* | 4/2013 | Shan | A61B 5/24 607/116 |
| 2013/0274867 A1* | 10/2013 | Bienvenu | A61L 31/18 623/1.34 |
| 2014/0094844 A1* | 4/2014 | Gulachenski | A61M 25/0012 606/200 |
| 2018/0178023 A1* | 6/2018 | Becklund | A61M 25/0082 |

\* cited by examiner

SINGLE AND MULTILAYER BANDS AND RELATED METHODS

RELATED APPLICATIONS

This application claims priority to U.S. Provisional Application No. 62/409,608, filed on Oct. 18, 2016 and titled, "Single and Multilayered Bands and Related Methods," which is hereby incorporated by reference in its entirety.

TECHNICAL FIELD

The present disclosure relates generally bands and to marker components for medical devices. Bands within the scope of this disclosure include bands comprising superelastic materials, bands comprising radiopaque materials, and bands comprising both superelastic and radiopaque materials. In some embodiments, the present disclosure describes marker bands for use with medical appliances, including elongate medical instruments.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
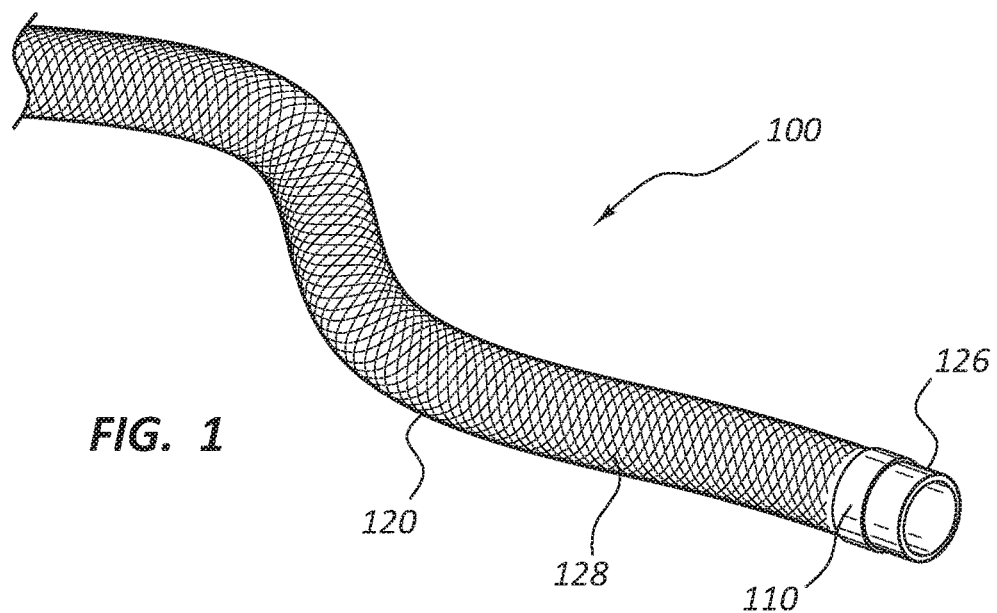
FIG. 1 is a perspective view of a medical appliance comprising a band coupled to an elongate tubular member.

Bands may be coupled to medical appliances to provide reinforcement and/or facilitate imaging of the medical appliance. For example, a band comprising a superelastic material may tend to return a medical appliance to a pre-set shape or configuration following deformation of the superelastic band. For example, a superelastic band coupled to the distal end of an elongate tubular member may facilitate flow through the elongate tubular member by tending to keep the distal end of the elongate tubular member open, including by recovering an open shape after being deformed or crushed by an outside force.

Marker components may be coupled to medical appliances to facilitate imaging of the medical appliance, thus facilitating deployment or placement of the medical appliance. Accordingly, marker components may comprise elements or features of a medical appliance which may be more readily imaged than other portions of the medical appliance. For example, many elongate medical devices are formed of polymers which may not have high radiopacity. A radiopaque marker band may thus be coupled to a polymeric elongate instrument to facilitate imaging of the polymeric elongate instrument.

Still further, in some instances, multilayer or composite bands may be used for both deformation recovery properties and to facilitate imaging. Accordingly, bands within the scope of this disclosure may comprise superelastic materials, radiopaque materials, or both.

Specific examples as used herein may refer to reinforcing bands and/or radiopaque marker components configured for use with tubular medical appliances. These specific examples should not be interpreted as limiting. The present disclosure is broad enough to include reinforcing members and marker components of various shapes and configurations, including arcuate shapes of less than 360 degrees, circular shapes, oval shapes, irregular shapes, and so forth. Disclosure discussed with respect to circular bands coupled to tubular devices may thus be analogously applied to other shapes of components coupled to medical appliances of various shapes.

Radiopaque marker bands may be positioned at an end of an elongate medical device to facilitate placement and imaging of the end of the device. Deformation of the radiopaque marker band (for example due to plastic deformation due to a radial crushing force) may interfere with flow through a lumen of the elongate medical device. A plastically deformed crushed band positioned at an otherwise open end of an elongate tubular member, for instance, may restrict flow through the end of the elongate tubular member.

Highly radiopaque metals may be used for radiopaque marker bands coupled to polymeric elongate medical devices. However, in some instances radiopaque maker bands comprised only of a single material may not exhibit a desired balance of material properties. For example, tantalum marker bands exhibit high radiopacity but tend to plastically deform when radially compressed. In other words, a tantalum marker band may be sufficiently radiopaque, but may crush down and impede flow into an elongate medical device. Nitinol, on the other hand, due to its superelastic properties, tends to return to a preset shape after it is radially compressed. Thus, a nitinol ring, temporarily crushed by a radial force, will return to a round shape when unconstrained, thus facilitating flow into an elongate medical device. However, nitinol does not exhibit the high degree of radiopacity of materials such as tantalum. Bands configured for deformation recover only, not necessarily to facilitate imaging, do not necessarily need high radiopacity.

Reinforcing members and marker components, including reinforcing band and marker bands, within the scope of this disclosure may comprise of two or more materials. In some instances, two materials may be coupled to each other forming a multilayered band. In such embodiments, one material may control certain properties of the multilayered band, while the other material may control other properties. For example, a first material may be selected based on its resilience, elasticity, or other mechanical properties while a second material may be selected based on its radiopacity. As used herein, a multilayer marker band wherein one material controls a property of the multilayer band indicates that the measured property would vary less than 10% when the multilayered band is tested as compared to testing the controlling material in the absence of other layers of the marker band. For example, a marker band may comprise a nitinol band coupled to a layer of a platinum iridium alloy. If the platinum iridium alloy "controls" the radiopacity of the band, the radiopacity would vary by less the 10% when platinum iridium layer is imaged alone as compared to imaging the combination of the nitinol band coupled to the platinum iridium layer.

Embodiments may be understood by reference to the drawings, wherein like parts are designated by like numerals throughout. Components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

FIG. 1 is a perspective view of a medical appliance 100 comprising a band 110 coupled to an elongate tubular member 120. In the illustrated embodiment, the elongate tubular member 120 comprises a reinforcing braid 128 disposed proximal of the band 110 and an unreinforced tip 126 distal of the band 110. Tubular members having different reinforcement structures or no reinforcement are within the scope of this disclosure.

The band 110 is disposed adjacent the distal end of the elongate tubular member 120, with a tip 126 extending distally of the band 110. In other embodiments, the band 110 may be disposed flush with the distal end of the elongate tubular member 120 such that no tip 126 extends distally beyond the band 110. Further, embodiments wherein a single band 110 is located along the length of the elongate tubular member 120, not necessarily adjacent the distal end, and embodiments comprising multiple bands 110 disposed along the elongate tubular member 120, are within the scope of this disclosure.

The band 110 may comprise a radiopaque marker band configured to facilitate imaging, a superelastic band configured to provide deformation recovery properties to the medical appliance 100, or may be configured to provide superelastic properties and high radiopacity. Radiopaque bands disposed adjacent a distal end of a elongate tubular member 120 may facilitate imaging and placement of the distal end of the elongate tubular member 120 and superelastic bands may aid in maintaining an open flow path through the distal end of the elongate tubular member 120.

Figure 2A:
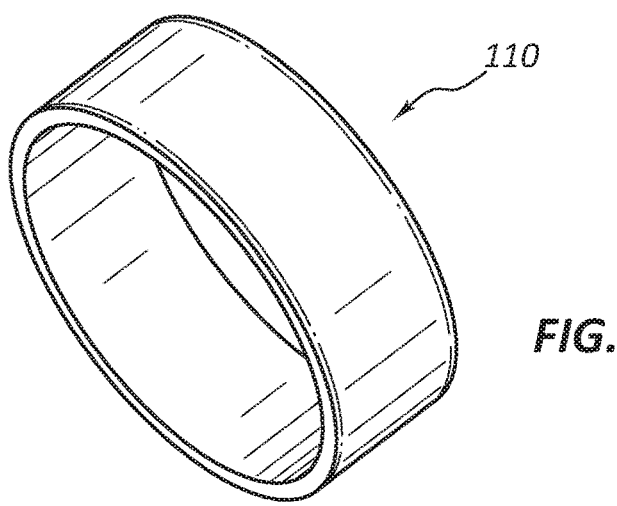
FIG. 2A is a perspective view of the band of FIG. 1.

FIG. 2A is a perspective view of the band 110 of FIG. 1. With reference to FIGS. 1 and 2A, in some embodiments, the band 110 may be coupled to an outside surface of the elongate tubular member 120. For example, the band 110 may be bonded to the elongate tubular member 120 by an adhesive. In other embodiments, the band 110 may be closely sized with the outside diameter of the elongate tubular member 120 and applied to the elongate tubular member 120 when the material of the elongate tubular member 120 is in a soft or tacky state due to melting, a solvent, or a pre-set state of the material comprising the elongate tubular member 120. The band 110 may thus bond to elongate tubular member 120 as the tacky surface cures or cools. Still further, the band 110 may be placed by reflow or melting into the surface of the elongate tubular member 120 or may be placed on a mandrel while the polymer material of the elongate tubular member 120 is extruded over top of the band 110.

Figure 2B:
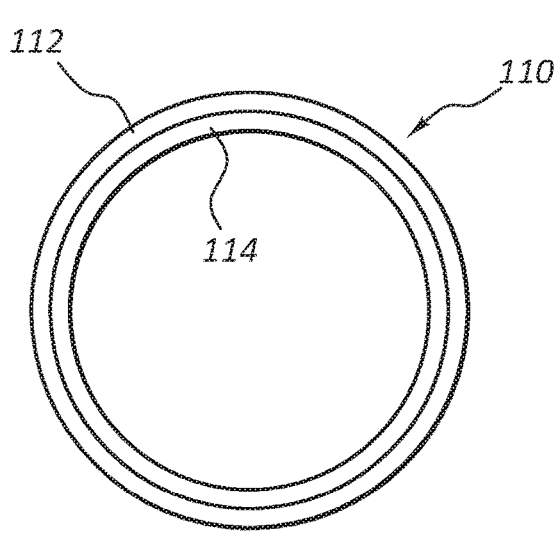
FIG. 2B is a front elevation view of the band of FIG. 1 schematically showing a two layer design.

FIG. 2B is a front elevation view of the band 110 of FIG. 1 schematically showing a two layer design. Specifically, in the view of FIG. 2B, a first, outer layer 112 and a second, inner layer 114 of the band 110 are indicated as shown. As discussed above, in some embodiments, the outer layer 112 and the inner layer 114 may comprise different materials. In such embodiments, the material of the outer layer may control one or more properties of the marker band 110 and/or the inner layer may control one or more properties of the marker band 100.

In some embodiments, the outer layer 112 may be configured to control the mechanical properties of the band 110. For example, the outer layer 112 may comprise a superelastic material such as a nitinol ring shape set into the circular configuration shown in FIG. 2B. Though nitinol is used in specific examples herein as an example of superelastic material, other superelastic materials, including shape memory polymers are within the scope of this disclosure. Superelastic materials tend to return to the preset shape after deformation. In embodiments where the outer layer 112 controls the mechanical properties, the inner layer 114 may return to the circular configuration shown due to its coupling to the outer layer, even if the material of the inner layer 114 would tend to plastically deform when crushed (if it were not coupled to the outer layer 112). In other words, internal forces acting within the outer layer 112 to return it to a shape set configuration after deformation may be sufficient to also return the coupled inner layer 114 to that configuration, even though the material of the inner layer 114 may tend to resist the return to that configuration.

In some embodiments, the inner layer 114 may comprise a material having a greater radiopacity than the outer layer 112. In some such embodiments, the inner layer 114 may also control the radiopacity of the band 110.

Multilayer bands, such as marker band 110 of FIG. 2B, may thus exhibit the radiopacity of one material layer and the mechanical properties of another layer. In this way, a band 110 may return to an open shape in a superelastic manner, while exhibiting radiopacity greater than superelastic materials.

In some embodiments the outer layer 112 may comprise nitinol or some other superelastic material. The inner layer 114 may comprise a layer of radiopaque material deposited on an inside surface of the nitinol outer layer 112. In some embodiments, the inner layer 114 may comprise a platinum iridium alloy deposited on the nitinol outer layer 112. Various platinum iridium alloys are within the scope of this disclosure including alloys containing 90% platinum and 10% iridium.

Still further, the inner layer 114 may comprise a flat wire or ribbon of material coupled to an inside surface of the outer layer 112. The flat wire or ribbon may have the same width (measured in the longitudinal direction of elongate tubular member 120) as the outer layer 112, or multiple wraps of a flat wire or ribbon having a smaller width than the outer layer may be positioned adjacent each other to cover the entire inside surface of the outer layer 112. These wraps may or may not overlap in the width direction. Additionally, the inner layer 114 may comprise a ribbon of material that extends around the inside surface of the outer layer 112 such that it overlaps itself to create an inner layer 114 with a greater thickness than a single layer of ribbon material. For example, an inner layer 114 may comprise a ribbon having the same width as the outer layer 112. The ribbon of material may extend the first 360 degrees around the inside surface of the outer layer 112 with the ribbon in direct contact with the inside surface of the outer layer 112. The ribbon material may then overlap itself along an additional arc (such as for an additional 90 degrees or 180 degrees) or along multiple full circles of 360 degrees.

An inner layer 114 comprising a flat wire ribbon may be mechanically fastened to an inside surface of the outer layer 112 or may simply be placed adjacent the outer layer 112 and the two components disposed between layers of an elongate tubular member in order to couple the components together.

FIG. 2B shows the outer layer 112 and the inner layer 114 as having the same, or similar, thicknesses. FIG. 2B is schematic in nature, and is not intended to indicate the relative thicknesses of the outer layer 112 and the inner layer 114. Any relative thickness of these layers is within the scope of this disclosure.

Figure 2C:
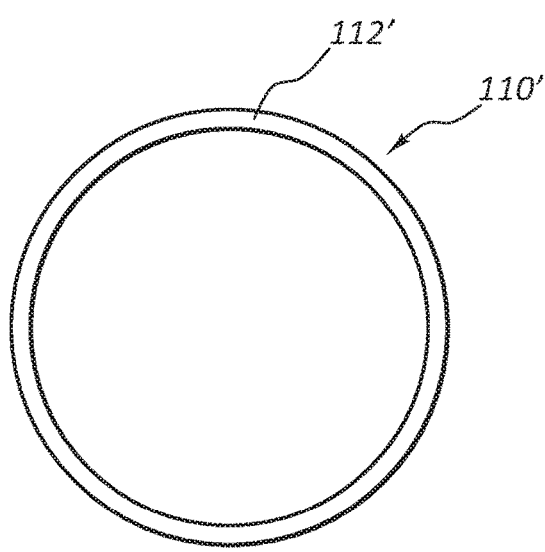
FIG. 2C is a front elevation view of another embodiment of a band schematically showing a single layer design.

FIG. 2C is a front elevation view of another embodiment of a band 110' schematically showing a single layer design. Accordingly, a single layer 112' is indicated by a reference numeral in the drawing. As discussed above, a single layer band, such as band 110', comprising a superelastic material may be configured to impart superelastic properties, including deformation or crush recovery, to a medical appliance. The single layer band 110' does not necessarily exhibit high radiopacity.

With reference to FIGS. 2A-2C, bands within the scope of this disclosure (whether single layer or multilayered) may be formed in a variety of sizes depending on application. In some instances bands may be between 0.020 inches and 0.060 inches wide (measured along the longitudinal direction of a elongate tube to which the band is configured to be coupled), including between 0.030 inches and 0.050 inches wide. Bands may be between 0.002 inches and 0.008 inches thick (measured in the radial direction) including all layers. In some embodiments, a multilayered band may comprise a superelastic layer between 0.002 inches and 0.006 inches thick and a radiopaque layer between 0.001 inches and 0.002 inches thick. One exemplary multilayered band comprising a nitinol layer between 0.002 inches and 0.006 inches thick and a platinum irridium alloy layer between 0.001 inches and 0.002 inches thick exhibited high radiopacity and high deformation recovery properties.

Further, the discussion above is based on embodiments wherein the outer layer 112 controls the mechanical properties of the marker band 110 and the inner layer 114 is more radiopaque than the outer layer 112. A reversal of these properties, that is, when the inner layer 114 controls the mechanical properties and/or the outer layer 112 is more radiopaque than the inner layer 114 are likewise within the scope of this disclosure. Further, embodiments wherein three, four, or more layers comprise the marker band 110 are within the scope of this disclosure. Additionally, the outer layer 112 and/or the inner layer 114 may comprise one or more sublayers each.

Figure 3:
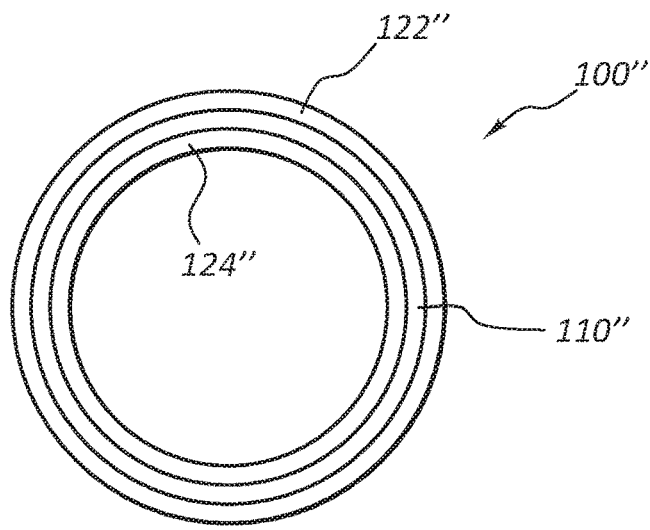
FIG. 3 is a front elevation view of a band coupled to an elongate tubular member.

FIG. 3 is a front elevation view of a medical appliance 100" comprising a band 110" coupled to an elongate tubular member (comprised of outer layer 122" and inner layer 124"). In the embodiment shown in FIG. 1, the band 110 is coupled to an outside diameter of the elongate tubular member 120. In the embodiment of FIG. 3, the band 110" is disposed between an outer layer 122" and an inner layer 124" of an elongate tubular member. Such embodiments may create a medical appliance 100" having a smooth interior and exterior surface.

Figure 4A:
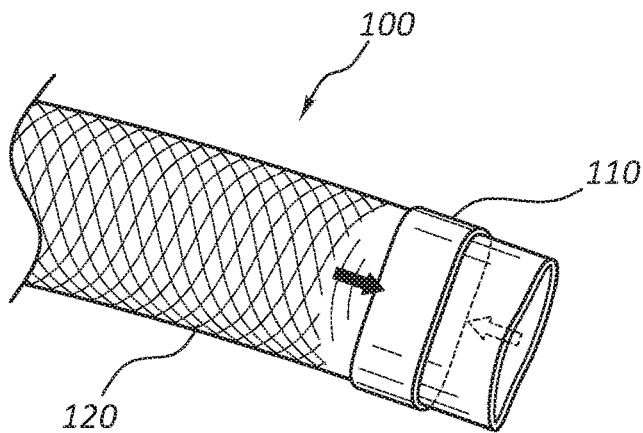
FIG. 4A is a perspective view of the band and elongate tubular member of FIG. 1 in a radially constrained state.
Figure 4B:
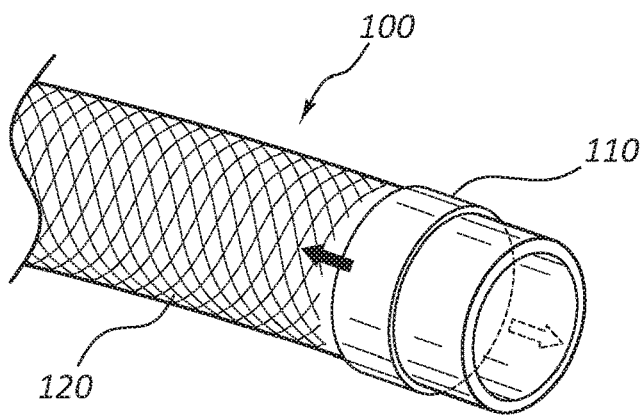
FIG. 4B is a perspective view of the band and elongate tubular member of FIG. 4A in a radially unconstrained state.

FIG. 4A is a perspective view of the medical appliance 100 of FIG. 1 showing the band 110 in a radially constrained state. FIG. 4B is a perspective view of the medical appliance 100 of FIG. 4A in a radially unconstrained state. The arrows in FIG. 4A illustrate a crush force that may be applied to the band 110 during deployment or use. For example, the medical appliance 100 may be radially constrained during deployment. Similarly, during use, bodily structures may act on the band to radially constrain or crush it. The arrows in FIG. 4B illustrate internal forces generated by the superelastic properties of the band 110 which return it to the open and round configuration when unconstrained.

Methods of constructing a medical appliance 100 as described above are within the scope of this disclosure. Methods of coupling one or more layers (112, 114) of a band 110 to each other, and methods of coupling a band 110 to an elongate tubular member 120 are also within the scope of this disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A medical device comprising:
an elongate tubular member defining a lumen; and
a band coupled to the elongate tubular member, the band consisting of a band outer layer controlling a mechanical properties of the band and a band inner layer controlling a radiopacity of the band;
wherein the band inner layer covers an entire inside surface of the band outer layer,
wherein the band outer layer comprises a superelastic material,
wherein the elongate tubular member comprises an outer layer and an inner layer, and wherein the band is disposed between the outer layer of the elongate tubular member and the inner layer of the elongate tubular member such that the medical device comprises a smooth interior and exterior surface,
wherein the elongate tubular member covers an entire inside surface of the band inner layer,
wherein the band outer layer covers an entire outside surface of the band inner layer,
wherein the band inner layer comprises a flat wire ribbon mechanically coupled to the band outer layer,
wherein the flat wire ribbon is a continuous piece of material that comprises an overlapping portion and a non-overlapping portion,
wherein the overlapping portion comprises at least two layers of the flat wire ribbon in direct contact with each other, and
wherein the overlapping portion is thicker than the non-overlapping portion.

2. The medical device of claim 1, wherein the band inner layer comprises a material deposited on the inside surface of the band outer layer.

3. The medical device of claim 1, wherein the flat wire ribbon has a thickness between 0.001 and 0.002 inches.

4. The medical device of claim 3, wherein the band outer layer has a thickness between 0.002 and 0.006 inches.

5. The medical device of claim 1, wherein the overlapping portion comprises an overlap of from one degree to 360 degrees.

6. The medical device of claim 1, wherein the overlapping portion comprises a plurality of 360 degree overlaps.

7. A medical device comprising:
an elongate tubular member defining a lumen; and
a band coupled to the elongate tubular member, the band comprising a band outer layer controlling a mechanical properties of the band and a band inner layer controlling a radiopacity of the band;
wherein the band inner layer covers an entire inside surface of the band outer layer,
wherein the band outer layer comprises a superelastic material,
wherein the elongate tubular member comprises an outer layer and an inner layer, and wherein the band is disposed between the outer layer of the elongate tubular member and the inner layer of the elongate tubular member,
wherein the elongate tubular member covers an entire inside surface of the band inner layer,
wherein the band outer layer covers an entire outside surface of the band inner layer,
wherein the band inner layer comprises a flat wire ribbon mechanically coupled to the band outer layer, the flat wire ribbon is a continuous piece of material comprising an overlapping portion that comprises two layers of the flat wire ribbon in direct contact with each other and a non-overlapping portion comprising a single layer of the flat wire ribbon, and
wherein the overlapping portion is thicker than the non-overlapping portion.

8. The medical device of claim 1, wherein the band inner layer defines a lumen such that the band outer layer is disposed outside the lumen and the band inner layer.

9. The medical device of claim 7, wherein the band inner layer defines a lumen such that the band outer layer is disposed outside the lumen and the band inner layer.

* * * * *